US008147553B2

(12) United States Patent
Vresilovic et al.

(10) Patent No.: US 8,147,553 B2
(45) Date of Patent: Apr. 3, 2012

(54) SUPPLEMENTATION OR REPLACEMENT OF A NUCLEUS PULPOSUS OF AN INTERVERTEBRAL DISC

(75) Inventors: Edward Vresilovic, Ardmore, PA (US); Michael F. Keane, Downingtown, PA (US); Thomas P. Schaer, Landenberg, PA (US)

(73) Assignee: Synthes USA, LLC, West Chester, PA (US)

(*) Notice: Subject to any disclaimer, the term of this patent is extended or adjusted under 35 U.S.C. 154(b) by 387 days.

(21) Appl. No.: 12/163,407

(22) Filed: Jun. 27, 2008

(65) Prior Publication Data

US 2008/0312744 A1 Dec. 18, 2008

Related U.S. Application Data

(62) Division of application No. 11/189,753, filed on Jul. 27, 2005, now abandoned.

(60) Provisional application No. 60/591,094, filed on Jul. 27, 2004.

(51) Int. Cl.
*A61F 2/44* (2006.01)

(52) U.S. Cl. .................................... 623/17.16

(58) Field of Classification Search ..... 623/17.11–17.16
See application file for complete search history.

(56) References Cited

U.S. PATENT DOCUMENTS

| 5,047,055 A | 9/1991 | Bao et al. |
| 5,192,326 A | 3/1993 | Bao et al. |
| 5,556,429 A | 9/1996 | Felt |
| 5,824,093 A | 10/1998 | Ray et al. |
| 5,919,235 A | 7/1999 | Husson et al. |
| 5,976,186 A | 11/1999 | Bao et al. |
| 6,132,465 A | 10/2000 | Ray et al. |
| 6,187,048 B1 | 2/2001 | Milner et al. |
| 6,224,630 B1 | 5/2001 | Bao et al. |
| 6,264,495 B1 | 7/2001 | Robertson et al. |

(Continued)

FOREIGN PATENT DOCUMENTS

FR 2712486 5/1995

(Continued)

OTHER PUBLICATIONS

Nakai et al. "Anterior transvertebral herniotomy for cervical disk herniation", J Spinal Disord, Feb. 2000; 13(1): 16-21.

(Continued)

*Primary Examiner* — Eduardo C Robert
*Assistant Examiner* — Summer Kostelnik
(74) *Attorney, Agent, or Firm* — Stradley Ronon Stevens & Young LLP

(57) ABSTRACT

A degenerated nucleus pulposus located in a central core region of an intervertebral disc within the annulus fibrosus is supplemented or replaced by a method wherein an amount of a biocompatible material is introduced into the central core region by a process including the steps of 1) forming a channel through a vertebral body adjacent to said intervertebral disc, extending from an exterior surface of the vertebral body to the central core region of the annulus fibrosus; 2) introducing an amount of a biocompatible material through the channel into the central core region of the annulus fibrosus; 3) pressurizing the biocompatible material through the channel to a postsurgical pressure sufficient to alleviate symptoms caused by the degenerated nucleus pulposus; and 4) sealing the channel while maintaining the sufficient postsurgical pressure. After sealing the channel, a vertebroplasty may optionally be performed in the vertebra.

51 Claims, 4 Drawing Sheets

U.S. PATENT DOCUMENTS

| | | |
|---|---|---|
| 6,264,659 B1 | 7/2001 | Ross et al. |
| 6,280,475 B1 | 8/2001 | Bao et al. |
| 6,558,390 B2 | 5/2003 | Cragg |
| 6,602,291 B1 | 8/2003 | Ray et al. |
| 6,607,530 B1 | 8/2003 | Carl et al. |
| 6,620,196 B1 | 9/2003 | Trieu |
| 6,740,090 B1 | 5/2004 | Cragg et al. |
| 6,790,210 B1 | 9/2004 | Cragg et al. |
| 6,793,656 B1 | 9/2004 | Mathews |
| 6,923,811 B1 | 8/2005 | Carl et al. |
| 6,974,479 B2 | 12/2005 | Trieu |
| 7,008,431 B2 | 3/2006 | Simonson |
| 7,198,047 B2 | 4/2007 | Lambrecht et al. |
| 7,214,245 B1 | 5/2007 | Marcolongo et al. |
| 2002/0173796 A1 | 11/2002 | Cragg |
| 2003/0199979 A1 | 10/2003 | McGuckin, Jr. |
| 2004/0111161 A1 | 6/2004 | Trieu |
| 2004/0220296 A1 | 11/2004 | Lowman et al. |
| 2004/0228853 A1 | 11/2004 | Serhan et al. |
| 2004/0229786 A1 | 11/2004 | Attawia et al. |
| 2004/0229878 A1 | 11/2004 | DiMauro et al. |
| 2004/0247867 A1* | 12/2004 | Chaouk et al. ............ 428/364 |
| 2005/0025765 A1 | 2/2005 | DiMauro et al. |
| 2005/0055099 A1 | 3/2005 | Ku |
| 2005/0071012 A1 | 3/2005 | Serhan et al. |
| 2005/0119750 A1 | 6/2005 | Studer |
| 2006/0100304 A1 | 5/2006 | Vresilovic et al. |
| 2007/0106387 A1 | 5/2007 | Marcolongo et al. |

FOREIGN PATENT DOCUMENTS

| | | |
|---|---|---|
| WO | WO 00/67650 | 11/2000 |

OTHER PUBLICATIONS

Joshi Abhijeet Bhaskar, Dissertation Thesis "Mechanical Behavior of Lumbar Intervertebral Disc with Polymeric Hydrogel Nucleus Implant: An Experiment and Finite Element Study", Drexel University Feb. 2004.

D. Grob et al., "Direct pediculo-body fixation in cases of spondylolisthesis with advanced intervertebral disc degeneration", Eur. Spine J, 5, 281-285.

Gruber et al. "Recent Advances in Disc Cell Biology", Spine 28(2) 2003.

Liu, et al. "Nitric Oxide Mediates the Change of Proteoglycan Synthesis in the Human Lumbar Intervertebral Disc in Response to Hydrostatic Pressure", Spine 26(2), 134-141 2001.

Handa, et al. "Effects of Hydrostatic Pressure on Matrix Synthesis and Matrix Metalloproteinase Production in the Human Lumbar Intervertebral Disc", Spine 22(10), 1085-1091 1997.

Wilke, et al. "Anatomy of the Sheep Spine and Its Comparison to the Human Spine", The Anatomical Record, 247:542-555 (1997).

Joshi, et al. "Nucleus Implant Parameters Significantly Change the Compressive Stiffness of the Human Lumbar Intervertebral Disc", Transactions of the ASME 127, 536-540 2005.

Bone Cement, IRC Interdisciplinary Research Center in Biomedical Materials, http://www.irc-biomed-materials.qmul.ac.uk.

* cited by examiner

SUPPLEMENTATION OR REPLACEMENT OF A NUCLEUS PULPOSUS OF AN INTERVERTEBRAL DISC

CROSS-REFERENCE TO RELATED APPLICATION

This application is a division of U.S. patent application Ser. No. 11/189,753, filed Jul. 27, 2005, now abandoned which claims the benefit of U.S. Provisional Patent Application No. 60/591,094, filed Jul. 27, 2004, the entire disclosures of which are incorporated herein by reference.

BACKGROUND OF THE INVENTION

1. Field of the Invention

The present invention relates to methods and apparatus for replacing or supplementing the natural nucleus pulposus of an intervertebral disc by using a viscoelastic low-modulus implant through a transosseus approach, and more particularly to methods and apparatus for pressurizing a viscoelastic implant within the intervertebral disc to achieve an appropriate physiologic state of annulus tension and nucleus pressurization.

2. Brief Description of the Prior Art

Chronic back pain, typically lower back pain, is experienced by many individuals, and is responsible for much lost time at work and expense for treatment. Such pain is generally the result of a pathological condition of an intervertebral disc, caused by injury or age-related degeneration.

Current treatment options for lower back pain range from conservative bed rest to highly invasive surgical procedures including spinal fusion and discectomy. Spinal fusion, i.e., fusion or immobilization of the vertebrae on each side of the afflicted intervertebral disc, is a procedure that offers pain relief and an increased stability of the fused segment. Discectomy, i.e., surgical removal of part of the intervertebral disc is another surgical option.

Total disc replacement with a mechanical prosthesis has been proposed as another option for relief of back pain, and a number of such mechanical prosthesis have been proposed.

The human intervertebral disc is comprised of two major structures, an inner gelatinous nucleus pulposus and an outer tendinous structure, the annulus fibrosis. Degeneration of the nucleus leads to degradation and loss of function of the intervertebral disc, resulting in pain and disability. Consequently, another surgical option for the relief of lower back pain is replacement of the nucleus, leaving the annulus intact. Thus, the aim of nucleus replacement is to relieve pain, to restore healthy physiologic function to the disc, and to prevent additional wear on the annulus.

Normal disc function requires the combined action of the nucleus pulposus and annulus fibrosus. Consequently, a nucleus implant should preferably tend to restore the normal mobility of the disc, restore the disc height and re-create healthy disc pressure in order to place the annulus fibers back into their natural state of tension.

Accordingly, a need exists for a nucleus replacement device and a method of implantation that substantially reproduces the synergistic interaction between the nucleus and annulus, thus restoring the normal mechanical properties and mobility of the disc.

SUMMARY OF THE INVENTION

According to the present invention a degenerated nucleus pulposus contained within a central core of an annulus fibrosus of an intervertebral disc can be replaced or supplemented by a procedure that includes:

1) forming a channel through a vertebral body adjacent to the intervertebral disc, the channel extending from an exterior surface of the vertebral body to the central core of the annulus fibrosus;
2) introducing an amount of a biocompatible material through the channel into the central core of the annulus fibrosus;
3) pressurizing the biocompatible material through the channel to a physiologic pressure sufficient to alleviate symptoms caused by the degenerated nucleus pulposus; and
4) sealing the channel while maintaining the pressure.

Accordingly, in one aspect of the present invention a method is provided for replacing or supplementing a degenerated nucleus pulposus.

In another aspect, the invention provides a method for introducing a biocompatible material into the central core of an annulus fibrosus of an intervertebral disc.

In another aspect, the invention provides a method for introducing a hydrogel or other relatively low-modulus material into the central core of an annulus fibrosus of an intervertebral disc.

In another aspect, the invention provides a method for introducing a pressurized implant into the central core of an annulus fibrosus of an intervertebral disc.

In another aspect, the invention provides a surgical approach to the nucleus for implantation of an implant that will prevent damage to the annulus.

In another aspect, the invention provides a transosseus approach to the nucleus through the superior or inferior vertebral bodies.

In another aspect, the invention provides a method of closing a channel in the vertebral body that will compress a nucleus replacement into the central core of the annulus fibrosus to ensure complete filling of the core.

In another aspect, the invention provides a replacement or supplement for the nucleus of the natural intervertebral disc that is designed to work synergistically with the annulus to reproduce normal disc mechanics.

In another aspect, the invention provides a postsurgical configuration of a replaced or supplemented nucleus pulposus that can reproduce, at least approximately, the mechanical properties of the normal human intervertebral disc.

In another aspect, the invention provides an implant that can improve the function of a degenerated nucleus pulposus of an intervertebral disc.

Additional aspects of the invention will be apparent from the description of the invention that follows.

DETAILED DESCRIPTION OF THE INVENTION

Figure 1:
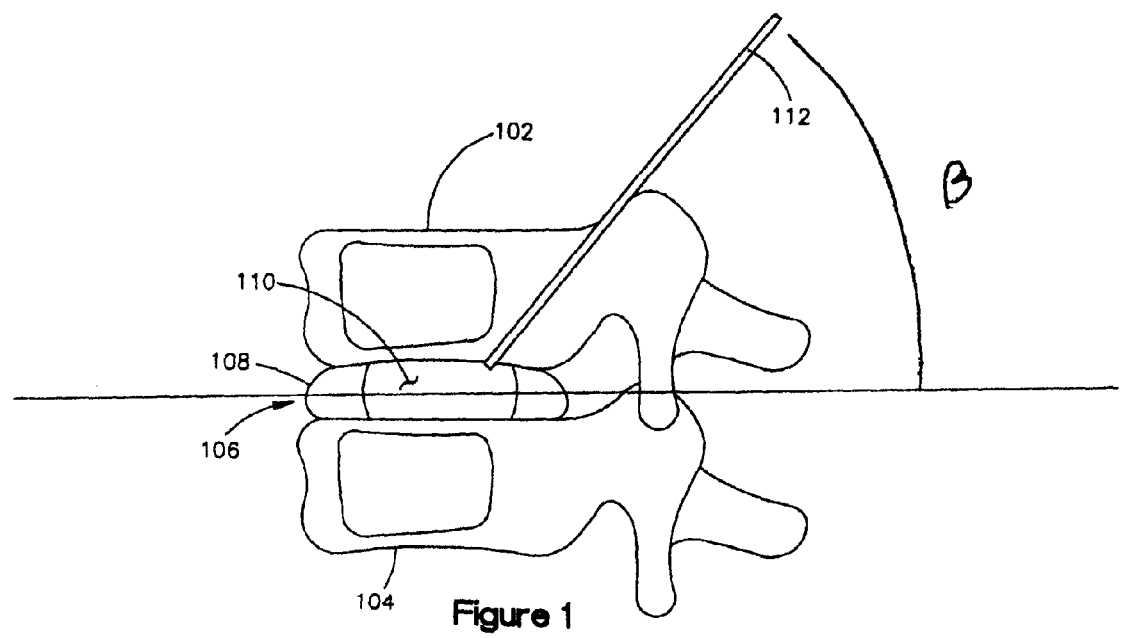
FIG. 1 is a lateral elevational cross-section of the functional spinal motion unit of a human spine, i.e., intervertebral disc with superior and inferior vertebrae, illustrating the first step in the transosseus approach of the invention, i.e., drilling an access path with a guide wire.

According to the invention, an implant that supplements or replaces the nucleus pulposus of an intervertebral disc is implanted by a transosseous approach through an adjacent vertebra.

In a preferred mode the method of the invention includes the steps of:
1) forming a channel through a vertebral body adjacent to the intervertebral disc, the channel extending from an exterior surface of the vertebral body to the central core of the annulus fibrosus;
2) introducing an amount of a biocompatible material through the channel into the central core of the annulus fibrosus;
3) pressurizing the biocompatible material through the channel to a physiologic pressure sufficient to alleviate symptoms caused by the degenerated nucleus pulposus; and
4) sealing the channel while maintaining the pressure.

In a preferred embodiment of the invention, a relatively soft, low-modulus implant (i.e., having a low unconstrained compression modulus) is inserted and pressurized by a transosseous approach through an adjacent vertebra. The invention will be described below in terms of such a preferred embodiment; the skilled practitioner will recognize that the transosseous approach of the invention may be utilized to insert any appropriate prosthesis for a nucleus pulposus.

According to a preferred embodiment of the invention, in a first step, a channel is formed through a vertebra adjacent, i.e., immediately superior or inferior, to the intervertebral disc into which an implant is to be inserted. The transvertebral channel may be made by any conventional surgical technique for drilling through a bony structure such as a vertebra.

After the channel has been drilled, the surgical site is prepared, if necessary, by removing a portion or all of the natural nucleus pulposus. Such removal may be accomplished by conventional surgical techniques. Thereafter, an amount of a biocompatible material, preferably a relatively low-modulus material, is inserted through the transvertebral channel sufficient to fill the central core of the intervertebral disc and provide the necessary disc height and intervertebral disc pressure required to at least approximate the function of the natural intervertebral disc.

A preferred embodiment of a biocompatible material suitable for replacement or supplementation of a nucleus pulposus is a solid, substantially fully hydrated hydrogel as disclosed in copending U.S. patent application Ser. No. 11/134,309 by Vresilovic et al., filed May 23, 2005, the entire disclosure of which is incorporated herein by reference. Another preferred biocompatible material for use in the method of the invention is a thermogelling polymer that can be injected in a relatively fluid state to fill the cavity of a removed or degenerated nucleus pulposus and then transitions to a solid gel at body temperature, as disclosed in copending U.S. patent application Ser. No. 10/837,082, by Lowman et al., filed Apr. 30, 2004, the entire disclosure of which is incorporated herein by reference. Both of these materials can be used in the method of the invention to provide a prosthesis that replaces or supplements a natural nucleus pulposus and establishes a substantially physiologic pressure state within the intervertebral disc. Such biocompatible materials can replace or supplement a nucleus pulposus by substantially filling void volume in the nucleus region of an intervertebral disc independently of natural variations in the anatomy of a patient and can be precisely pressurized by the method of the invention using sealing member as described herein.

Further embodiments of biocompatible materials that can be delivered and pressurized by the method of the invention include materials that can serve as scaffolds for tissue engineered constructs, and can incorporate cells, growth factors and other biologic materials that can promote the regeneration of intervertebral disc structures such as the nucleus, annulus or vertebral endplate. Certain conventional materials usable for such constructs materials may be sufficiently fluid to be capable of implantation by the method of the invention, and may therefore be capable of being implanted while avoiding damage to the annulus fibrosus and minimizing the possibility of subsequent expulsion. Furthermore, inasmuch as in vitro studies by Liu et al., Spine 2001, Vol. 26, p. 134; Handa et al., Spine 1997, Vol. 22, p. 1085; and Gruber et al., Spine 2003, Vol. 28 (2), p. 186; the entire disclosures of which are incorporated herein by reference, have shown the sensitivity of disc cell function to pressure, the method of the invention can provide a procedure for the delivery of biologic functional prostheses while minimizing the danger of subsequent expulsion and providing for adjusting the post-implantation pressure to promote initiation and maintenance of cellular growth and function.

The inserted material is pressurized, or at least maintained under pressure, by inserting a sealing member into the transvertebral channel that seals the channel against leakage of the material. Accordingly, the sealing member may be inserted at the end of the implantation to maintain pressure exerted by the implantation apparatus, or the sealing member may itself exert pressure on the implanted material as it is advanced through the transvertebral channel to its final sealing position. In one preferred embodiment, the sealing member comprises a plug of bone cement followed by a mechanical plug that is advanced into the channel to exert an appropriate pressure on the material implanted in the central core. The mechanical plug may be a conventional surgical bone screw. Alternatively, the transvertebral channel may be sealed by a plug of bone cement or other biocompatible material followed by a barbed plug or wedge forced into the channel to provide the requisite intradiscal pressure. As an alternative to the bone cement or other biocompatible material, a bolus of material can be forced into the channel to pressurize the implant and the channel sealed, as above, with a bone screw, barbed plug, or the like. In another embodiment, the sealing element may be provided by a bone plug and/or screw or wedge made of an osteoconductive or inductive biomaterial.

As is well-known in the art, a conventional bone screw can be moved a precise distance axially dependent on the number of turns applied to the screw. The advancement per turn can be determined by the pitch of the screw. Thus, the use of such a screw makes it possible to adjust the pressure within the cavity accurately by advancing the distal end of the screw in a precise manner against the implanted biocompatible material. Various combinations of screw pitch, length, thread height, and distal end geometries can be selected to achieve the sensitivity required per turn and to minimize wear at the implant-screw interface.

The bone cement used in sealing the transvertebral channel may be any conventional biocompatible bone cement. Such bone cements include poly(methyl methacrylate), calcium phosphate, calcium sulfate, calcium carbonate, hydroxyapatite, and the like. Alternatively, a natural biomaterial can be used, such as an autograft, allograft or xenograft.

An additional embodiment of the method of the invention incorporates a vertebroplasty procedure performed after the implantation of the biocompatible material replacing or supplementing the nucleus. In this alternative embodiment, the nuclear region of the disc is accessed by the transosseous approach described above, nucleus material is removed, if desired, to form a cavity, a biocompatible material is implanted to replace or supplement the nucleus, and a relatively small sealing element, such as a small bone screw, is fixed in the cortical bone forming the shell of vertebral endplate. A substantially conventional vertebroplasty is then performed by making a cavity in the bone behind the screw by conventional procedures used in vertebroplasty, and the cavity so formed is filled with a conventional biocompatible bone filler. Such a method of nucleus replacement or supplementation followed by vertebroplasty may be desirable to provide the benefits of nucleus replacement to older patient populations in which the strength of the vertebral body has been compromised.

Figure 3:
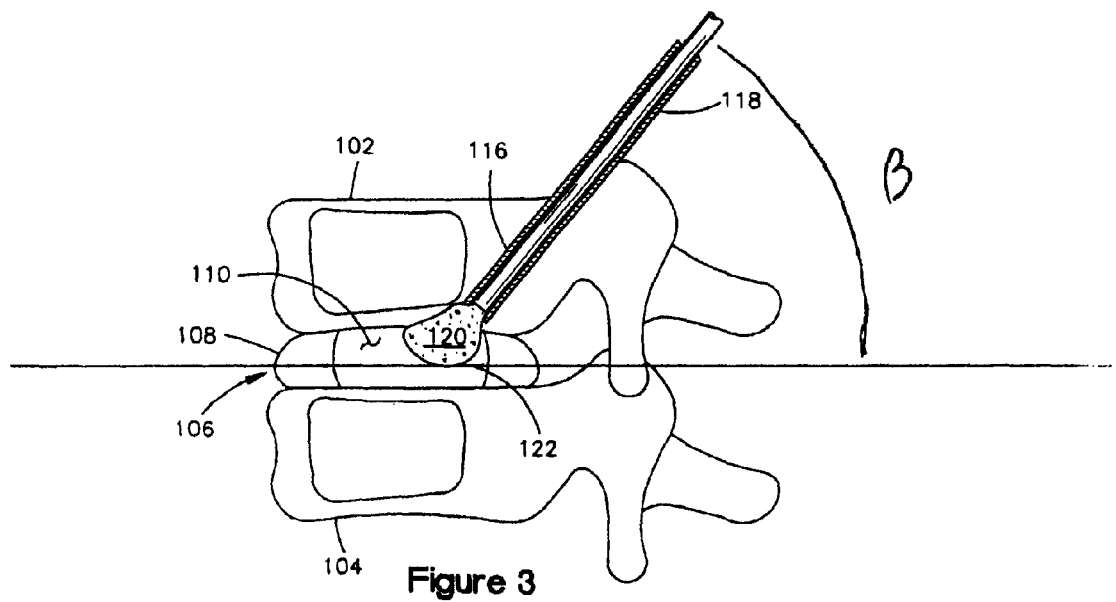
FIG. 3 is a cross-section of the functional spinal motion unit illustrating the third step in the transosseus approach, i.e., implantation of the implant through an insertion sheath.
Figure 4:
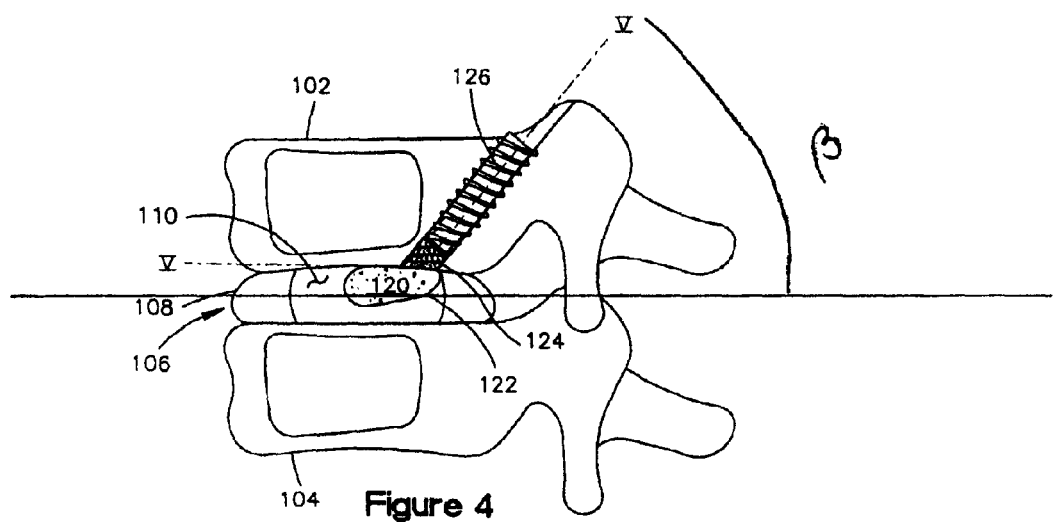
FIG. 4 is a cross-section of the functional spinal motion unit illustrating one embodiment of the third and fourth steps in the transosseus approach, i.e., backfilling and pressurizing the low-modulus material implant with a bone plug and screw.
Figure 5:
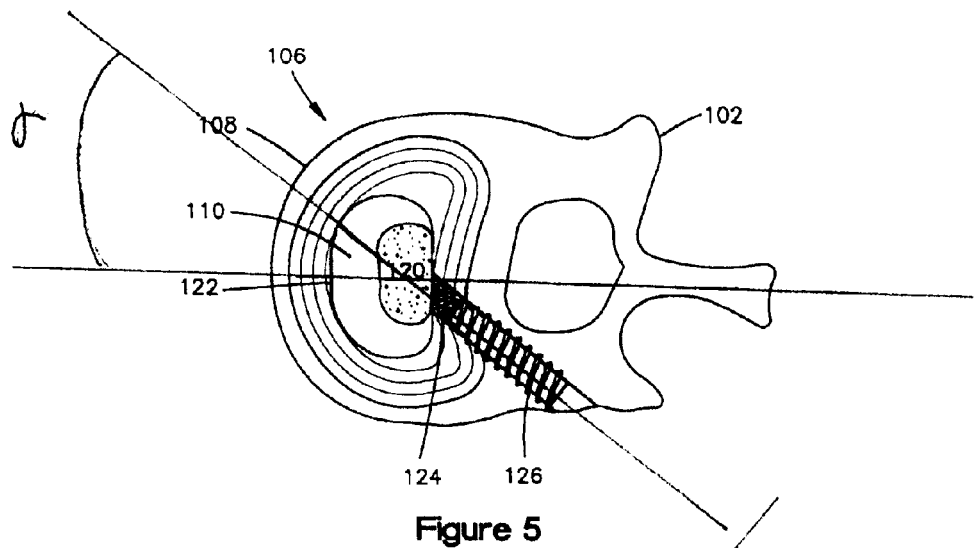
FIG. 5 is a transverse cross section of the functional spinal motion unit, again illustrating the third and fourth steps in the transosseus approach of the invention.

FIGS. 1-6 illustrate the practice of the invention to provide a pressurized implant within the central core of an intervertebral disc. FIGS. 1-4 and 6 are side elevational views, in partial cross-section, showing the implantation of a relatively low-modulus material into the central core of the intervertebral disc. FIG. 5 is a plan cross-sectional view, in partial cross-section, showing the implantation of the implant within the central core of the intervertebral disc.

Figure 2:
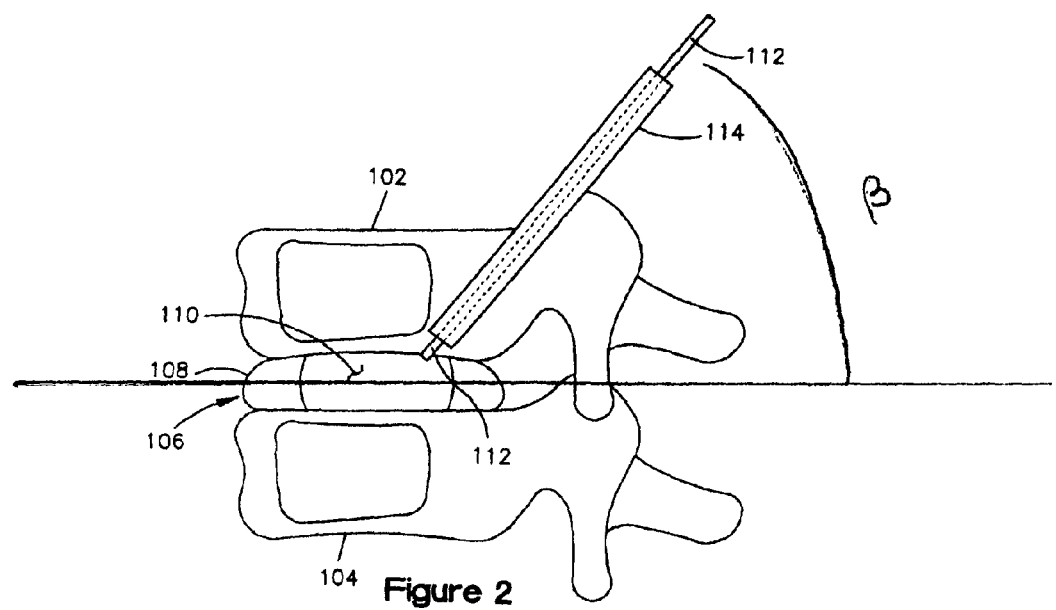
FIG. 2 is a cross-section of the functional spinal motion unit illustrating the second step in the transosseus approach, i.e., over-drilling with a cannulated drill bit.

FIGS. 1 and 2 illustrate schematically one procedure for formation of the transvertebral channel. FIG. 1 shows, in partial cross-section, a spinal motion segment or unit comprising a superior vertebra 102, an inferior vertebra 104 with an intervertebral disc, indicated generally at 106, having an annulus fibrosus 108 and a central core 110 that contains a nucleus pulposus. As an indication for the application of the method and prosthesis of the invention, the natural nucleus pulposus occupying the central core 110 will have experienced some pathological condition, such as degeneration, herniation, or the like, or will have been entirely or at least partially removed because of such a condition. FIG. 1 shows a first step wherein the path for the channel is defined by drilling with a guide wire 112 from the exterior of the vertebra 102 to the central core 110. FIG. 2 shows a second step wherein the guide wire 112 is overdrilled with a cannulated drill bit 114 to form a channel 116 extending into the central core 110. The central core 110 having been thus reached through the channel 116, the surgical site for receiving an implant is prepared within the central core 110 by conventional surgical procedures adapted to be conducted through the narrow channel 116. Referring to FIGS. 1-4 and 6, and as previously mentioned, preferably the channel is drilled through the superior or inferior vertebra (shown as superior vertebra) immediately adjacent to the intervertebral disc into which the implant is to be inserted. More preferably, the channel is drilled at a vertical acute angle β with respect to the endplates through which the channel is being formed. The vertical angle β being in a range from about 10° to about 70°, preferably from about 35° to about 45°, more preferably about 40°. Moreover, as shown in FIG. 5, the channel may also be drilled at a lateral angle α with respect to the patient's spinous process. The lateral approach angle α being in a range from about 20° to about 70°, preferably about 50°.

FIG. 3 shows the next step wherein a sheath 118 has been inserted into the channel 116, and an implant 120 is being passed through the sheath 118 into the central core 110.

Figure 6:
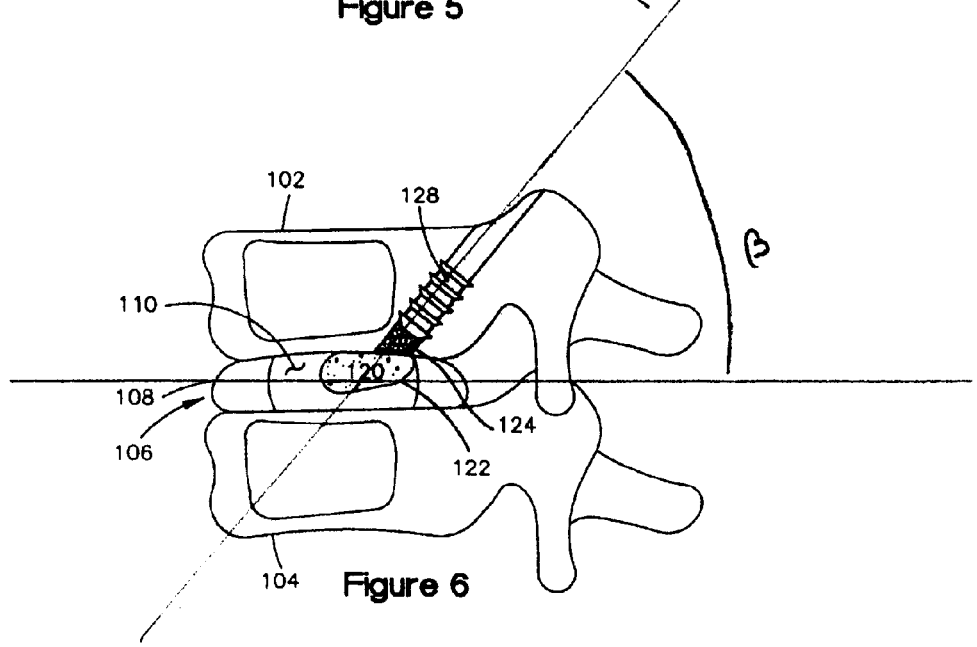
FIG. 6 is a cross section of the functional spinal motion unit illustrating another embodiment of the third and fourth steps in the transosseus approach, i.e., backfilling and pressurizing the low modulus implant with a wedge shaped implant.

FIGS. 4-6 illustrate the pressurization of the implant within the central core 110 of the intervertebral disc.

FIG. 4 shows a lateral cross-sectional view of an embodiment of the invention wherein a first quantity 122 of low-modulus material 120, e.g., a hydrogel, has been inserted into the central core 110. FIG. 5 shows a superior cross-sectional plan view of the spinal unit of FIG. 4 taken generally along the line V-V in FIG. 4. A bone screw 126 has been inserted into the channel to complete the insertion of the implant 120 into the central core 110 and seal the low-modulus material 120 therein under pressure. The bone screw 126 may extend entirely through the channel 116, or, as shown, it may extend into a portion of the channel 116 and exert its pressure through a second quantity of biocompatible sealing material 124, which may be, e.g., bone cement or another bolus of low-modulus material, remaining within the channel 116. The biocompatible sealing material can include such conventional biomaterials as an autograft, an allograft, or a xenograft.

FIG. 6 is a lateral cross-sectional view of another embodiment of the invention showing an alternative method of pressurizing and sealing the implant 120 within the central core 110 by driving an appropriate plug, e.g., a barbed plug 128, into the channel 116. Any other suitable plug, e.g., an expandable plug, or the like, can be used to seal the channel 116 and pressurize the implant 120 within the central core 110.

Any biocompatible material may be implanted according to the method of the invention. Preferably, the biocompatible material used to replace or supplement a degenerated nucleus pulposus is a is a low-modulus material, i.e., a material having a compressional modulus in the range from about 10 kPa to about 4 MPa, preferably from about 50 kPa to about 1 Mpa, and more preferably from about 100 kPa to about 200 kPa. The biocompatible low-modulus material preferably has a relatively high Poisson ratio in order to perform its function, as discussed below. Such a relatively high Poisson ratio is that within a range of about 0.30 to about 0.50, preferably from about 0.40 to about 0.50, and more preferably in the range from about 0.45 to about 0.50.

The biocompatible low-modulus material of the preferred embodiment of the invention may have any non-toxic biocompatible chemical composition. For example, silicone polymers, polyurethanes, and hydrogel materials, may be used. Such materials are known for use in implantable prostheses, and the practitioner can select a suitable material based on its known properties. A preferred low-modulus, high Poisson ratio material for implanting into the central core of the annulus fibrosus to replace or supplement the nucleus pulposus is a hydrogel such as a poly(vinyl alcohol)-poly (vinylpyrrolidone) (PVA-PVP) copolymer or an associating polymer blend such as a mixture of poly(vinyl alcohol) and poly(vinylpyrrolidone). Such a soft hydrogel, when compressed in one direction, will expand in directions generally at right angles to the direction of compression. This phenomenon, known as the Poisson effect, can effectively approximate the normal pressurization of the healthy liquid-like nucleus pressing against the inner wall of the surrounding annulus fibrosus during the various loading situations the disc encounters. Any biocompatible hydrogel or other low-modulus material capable of reproducing this effect is suitable for use in the method of the invention. Preferably, the biocompatible low-modulus material will have a compressional modulus not greater than about 4 Mpa, and within the range defined above. Other suitable hydrogel polymers, for example, include those disclosed in Ray et al., U.S. Pat. No. 6,132,465; Ray et al., U.S. Pat. No. 6,602,291; Bao et al, U.S. Pat. No. 5,976,186; Bao et al., U.S. Pat. No. 6,280,475; Marcolongo et al., U.S. patent application Ser. No. 10/111,782 (European Patent No. 1229873); Stoy, U.S. Pat. No. 6,264,495; Husson, U.S. Pat. No. 5,919,235; McGuckin, US Published Application No. 2003/0199979; Trieu, U.S. Pat. No. 6,620,196; Studer, PCT Published Application No. WO03/084444A1 and U.S. Published Patent Application No. 2005/0119750; and Breslave et al., French Patent 2712486, the entire disclosure of each of which is incorporated herein by reference.

The hydrogel or other low-modulus material may be introduced into the central core of the annulus fibrosus in any suitable form. A preferred configuration for the nucleus replacement or supplementary material is a thin cylindrical shape that can be inserted through a narrow channel less than 5 mm in diameter, such as a small hole drilled in an adjacent vertebra. Alternative preferred shapes for the inserted low-modulus material include a generally spherical shape or an ellipsoidal shape that can be inserted through a narrow channel, preferably less than about 5 mm in diameter. Curable materials that are introduced into the region of the nucleus pulposus and cure therein to form a low-modulus material are also implantable by the process of the invention, as well as associating polymers of the type disclosed in Marcolongo et al., U.S. patent application Ser. No. 10/111,782, referenced above.

The practice of the invention will be illustrated by the following example, which is intended to be illustrative and not limiting.

EXAMPLE

This example illustrates filling of a nucleus pulposus cavity in a spinal motion segment by the process of the invention. Various studies by the inventors have described the Poisson effect in a hydrogel and its usefulness in approximating the normal synergistic mechanical properties of the nucleus in interaction with the annulus. In order to achieve appropriate mechanical properties, proper filling of the disc core volume is essential.

Figure 7:
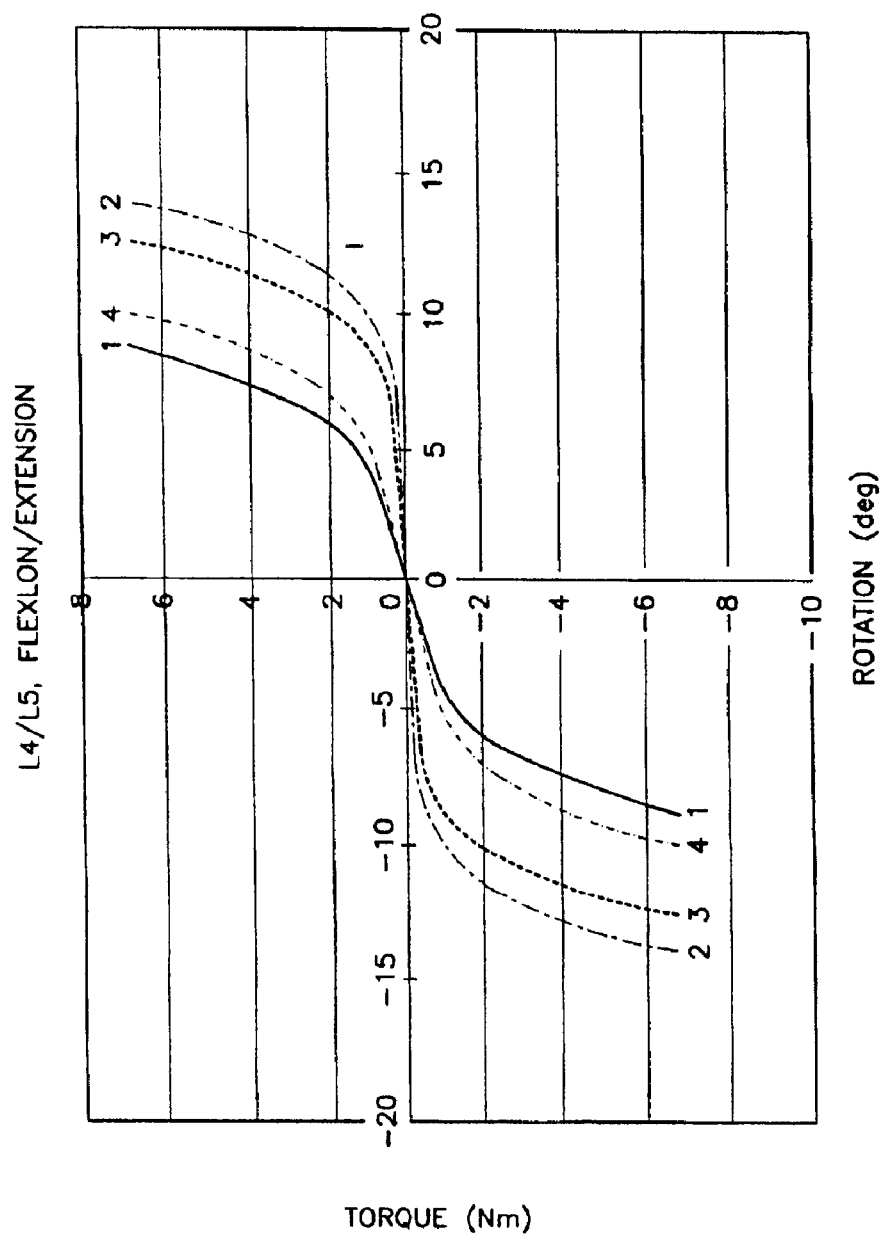
FIG. 7 shows the results of a series of flexion-extension tests conducted on a spinal motion segment implanted with a prosthesis by the process of the invention.

A flexibility experiment was conducted by performing the process of the invention for replacing the nucleus pulposus. The flexibility of the spinal motion segment or unit was measured at various steps in the procedure in order to illustrate the simulated degeneration and restoration of the nucleus. An appropriate specimen of an L4/L5 spinal motion segment was selected, including the L4 and L5 lumbar vertebrae and the intervertebral disc therebetween with intact annulus fibrosus and nucleus pulposus. The selected specimen had an essentially normal nucleus pulposus. The specimen was subjected to measurement of flexibility at four stages before, during, and after the nucleus replacement procedure by conducting a simulated flexion-extension series using pure moments. The torque required for a range of defined angles of flexion and extension was determined. The results are presented in the chart in FIG. 7, which shows torque v. degrees of rotation in flexion and extension.

The first of the four flexion-extension series was conducted on the intact healthy disc; the results are shown in Curve 1. The nucleus was then removed by a generally conventional procedure in which a trephine of suitable size is used to form an axial aperture in one of the adjacent vertebrae by removing a plug of bone, the nucleus is removed through the aperture so created, and the plug of bone is then reinserted and cemented in position to substantially restore the vertebral structure. Such a procedure is substantially similar to methods described by Joshi et al., Journal of Biomedical Engineering, June 2005, Vol 127; p 536-540, the entire disclosure of which is incorporated herein by reference. The specimen was then tested through the same applied moments. Accordingly, the second series simulates a severely degraded nucleus; the results are as shown in Curve 2. An access channel was then drilled through the upper vertebra of the specimen spinal motion unit and the specimen was implanted with a hydrogel implant in two stages. In the first stage the specimen was implanted with a hydrogel implant prepared as a thin string (diameter about 3 mm) inserted through a sheath inserted in the drilled channel in an amount that partially filled the volume left by the removal of the nucleus pulposus. The hydrogel was prepared according to the teachings of Marcolongo et al., U.S. Published Patent Application No. 2004/0220296. The partially restored spinal motion segment, thereby simulated a somewhat degenerated nucleus or a nucleus replaced without pressurization. When the spinal motion segment so restored was tested, a movement towards normal physiologic values over the range of motion was found, as shown in Curve 3. Finally, when the specimen was fully implanted with the hydrogel and the core was completely filled and pressurized, by inserting a bone screw according to the invention, close to full restoration of the disc mechanics was found, as shown in Curve 4.

The invention having now been described in terms of certain preferred embodiments it will be understood that modifications and changes can be made thereto without departing from the spirit and character thereof.

We claim:

1. A method for replacing or supplementing an intervertebral disc located between endplates of adjacent superior and inferior vertebral bodies, the endplates of the vertebral bodies each defining a longitudinal axis, the method comprising the steps of:
    (a) forming a channel through one of the superior and inferior vertebral bodies adjacent to the intervertebral disc, the channel extending from an exterior surface of the vertebral body to the intervertebral disc, the channel having a longitudinal axis defining a vertical approach angle with respect to the longitudinal axis of the endplate of the vertebral body through which the channel is formed, the vertical approach angle being in a range from about 10° to about 70°;
    (b) introducing a biocompatible material through the channel into the intervertebral disc; and
    (c) sealing the channel with a plug.

2. The method of claim 1, wherein the vertical approach angle is in a range from about 35° to about 45°.

3. The method of claim 1, wherein the vertical approach angle is about 40°.

4. The method of claim 1, wherein the longitudinal axis of the channel forms a lateral approach angle with respect to a spinous process plane of the adjacent superior and inferior vertebral bodies, the lateral approach angle being in a range from about 20° to about 70°.

5. The method of claim 4, wherein the lateral approach angle is about 50°.

6. The method of claim 1, wherein the plug is constructed of a biocompatible sealing material.

7. The method of claim 6, wherein the biocompatible sealing material is selected from the group consisting of a bone cement, an autograft, an allograft, and a xenograft.

8. The method of claim 7, wherein the bone cement is selected from the group consisting of poly(methylmethacrylate), calcium phosphate, calcium sulfate, calcium carbonate, and hydroxyapatite.

9. The method of claim 1, wherein the plug is comprised of a biocompatible sealing material and a mechanical plug.

10. The method of claim 9, wherein the mechanical plug is selected from the group consisting of a bone screw and a barbed plug.

11. The method of claim 1, further comprising the step of:
(d) inserting a predetermined quantity of a generally incompressible material in the channel between the biocompatible material and the plug.

12. The method of claim 11, wherein the generally incompressible material is selected from the group consisting of a bone cement, an autograft, an allograft, and a xenograft.

13. The method of claim 1, further comprising the step of:
(d) exerting pressure on the biocompatible material through the channel before sealing the channel.

14. The method of claim 13, wherein the biocompatible material in step (d) is pressurized by inserting a bone screw or a barbed plug into the channel.

15. The method of claim 1, wherein the biocompatible material has a compressional modulus not greater than about 4 Mpa.

16. The method of claim 1, wherein the biocompatible material has a Poisson ratio in a range of from about 0.30 to 0.50.

17. The method of claim 1, wherein the biocompatible material is a hydrogel.

18. The method of claim 17, wherein the hydrogel is a thin string.

19. The method of claim 1, wherein the biocompatible material is selected from the group consisting of a polyurethane and a silicone.

20. The method of claim 1 further comprising:
(a) forming an access space to from the posterior side of the spine to the pedicle region of one of the adjacent superior and inferior vertebral bodies.

21. The method of claim 20 wherein the channel is formed from the exterior surface in the vertebral bodies in the pedicle region of the vertebral body.

22. The method of claim 1, wherein the channel is formed through the superior vertebrae.

23. The method of claim 22, wherein the access space is formed from the posterior side of the spine.

24. The method of claim 23, wherein the channel is formed from the exterior surface of the pedicle region of the superior vertebral body.

25. The method of claim 1, wherein the biocompatible material is inserted into the channel at its entrance into the superior vertebral body.

26. The method of claim 1, wherein the channel is straight.

27. The method for replacing or supplementing a nucleus pulpous in an intervertebral disc having an annulus fibrosus surrounding a nucleus pulpous, the intervertebral disc being located between endplates of adjacent superior and inferior vertebral bodies, the endplates of the vertebral bodies each defining a longitudinal axis, the method comprising the steps of:
(a) forming a channel through one of the superior and inferior vertebral bodies adjacent to the intervertebral disc, the channel extending from an exterior surface of the vertebral body to the nucleus pulpous, the channel having a longitudinal axis defining a vertical approach angle with respect to the longitudinal axis of the endplate of the vertebra through which the channel is formed, the vertical approach angle being about 40°, the longitudinal axis of the channel forms a lateral approach angle with respect to a spinous process plane of the adjacent vertebral bodies, the lateral approach angle being about 50°;
(b) introducing an amount of biocompatible material through the channel into the annulus fibrosus; and
(c) sealing the channel with a plug.

28. The method of claim 27 wherein the channel extends from an exterior surface of the vertebral body in the region where the intervertebral disc does not contact the vertebral body to the nucleous pulpous in the intervertebral disc.

29. The method of claim 27, wherein the channel is formed from the exterior surface in the vertebral bodies in the pedicle region of the vertebral body.

30. The method of claim 27 wherein the channel is formed through the superior vertebrae.

31. The method of claim 30, wherein the access space is formed from the posterior side of the spine.

32. The method of claim 31, wherein the channel is formed from the exterior surface of the pedicle region of the superior vertebral body.

33. The method of claim 27, wherein the biocompatible material is inserted into the channel at its entrance into the superior vertebral body.

34. The method of claim 27, wherein the channel is straight.

35. A method for repairing an intervertebral disc located between endplates of adjacent superior and inferior vertebral bodies, the endplates of the vertebral bodies each defining a longitudinal axis, the method comprising the steps of:
(a) forming a channel through the superior vertebral body adjacent to the intervertebral disc, the channel extending from an exterior surface of the posterior or posterior—lateral side of the superior vertebral body down to the intervertebral disc, the channel having a longitudinal axis defining a vertical approach angle with respect to the longitudinal axis of the endplate of the vertebral body through which the channel is formed, the vertical approach angle being in a range from about 10° to about 70°;
(b) introducing a biocompatible material through the channel into the intervertebral disc; and
(c) sealing the channel with a plug.

36. The method of claim 35, wherein the vertical approach angle is in a range from about 35° to about 45°.

37. The method of claim 35, wherein the vertical approach angle is about 40°.

38. The method of claim 35, wherein the longitudinal axis of the channel forms a lateral approach angle with respect to a spinous process plane of the adjacent superior and inferior vertebral bodies, the lateral approach angle being in a range from about 20° to about 70°.

39. The method of claim 35, wherein the lateral approach angle is about 50°.

40. The method of claim 35, wherein the plug is constructed of a biocompatible sealing material.

41. The method of claim 40, wherein the biocompatible sealing material is selected from the group consisting of a bone cement, an autograft, an allograft, and a xenograft.

42. The method of claim 41, wherein the bone cement is selected from the group consisting of poly(methylmethacrylate), calcium phosphate, calcium sulfate, calcium carbonate, and hydroxyapatite.

43. The method of claim 35, wherein the plug is comprised of a biocompatible sealing material and a mechanical plug.

44. The method of claim 43, wherein the mechanical plug is selected from the group consisting of a bone screw and a barbed plug.

45. The method of claim 35, further comprising the step of:
   (d) inserting a predetermined quantity of a generally incompressible material in the channel between the biocompatible material and the plug.

46. The method of claim 35, further comprising the step of:
   (d) exerting pressure on the biocompatible material through the channel before sealing the channel.

47. The method of claim 46, wherein the biocompatible material in step (d) is pressurized by inserting a bone screw or a barbed plug into the channel.

48. The method of claim 35, wherein the biocompatible material has a compression modulus not greater than about 4 Mpa.

49. The method of claim 35, wherein the biocompatible material has a Poisson ratio in a range of from about 0.30 to 0.50.

50. The method of claim 35, wherein the biocompatible material is a hydrogel.

51. The method of claim 35, wherein the biocompatible material is selected from the group consisting of a polyurethane and a silicone.

* * * * *